United States Patent [19]

Meier et al.

[11] Patent Number: 4,796,846
[45] Date of Patent: Jan. 10, 1989

[54] RETAINING DEVICE FOR A SURGICAL INSTRUMENT

[75] Inventors: Hans Meier, Mellingen, Switzerland; Nash Aussenberg, New York, N.Y.

[73] Assignee: Automated Medical Products, Corporation, New York, N.Y.

[21] Appl. No.: 55,925

[22] Filed: Jun. 1, 1987

[51] Int. Cl.[4] .............................................. E04G 3/00
[52] U.S. Cl. .................................... 248/286; 248/287; 248/296; 269/328; 403/59; 403/80
[58] Field of Search ............... 248/286, 287, 284, 296, 248/298, 295.1; 269/328; 403/59, 80; 128/20

[56] References Cited

U.S. PATENT DOCUMENTS

| 3,046,072 | 7/1962 | Douglass, Jr. et al. | 269/328 |
| 3,339,913 | 9/1967 | Anderson | 248/298 |
| 4,018,412 | 4/1977 | Kees, Jr. et al. | 248/286 X |
| 4,143,652 | 3/1979 | Meir et al. | 128/20 |
| 4,491,435 | 1/1985 | Meir | 248/276 X |
| 4,547,092 | 10/1985 | Vetter et al. | 248/296 X |
| 4,602,756 | 7/1986 | Chatfield | 403/80 X |

*Primary Examiner*—Ramon O. Ramirez
*Attorney, Agent, or Firm*—Werner W. Kleeman

[57] ABSTRACT

The retaining device comprises a holder block operatively associated with a clamping mechanism. The retaining device is displaceably and selectively securable along a guide rail by means of the holder block. A surgical instrument is carried by a support rod which is axially movable up and down and positionally securable in the clamping mechanism. The arresting of the holder block at the guide rail and the support rod in the clamping mechanism is effected by a tensioning or tightening member, such as a tensioning nut or spider acting upon both the holder block and the support rod.

7 Claims, 4 Drawing Sheets

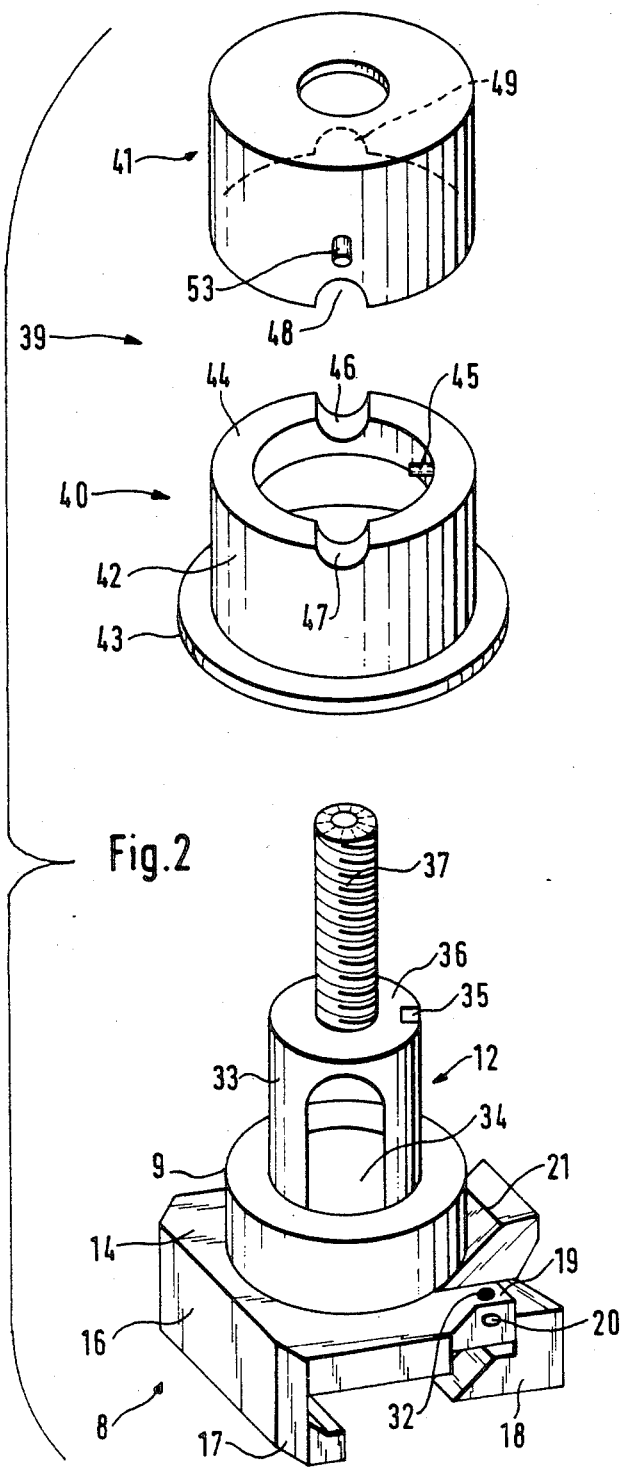

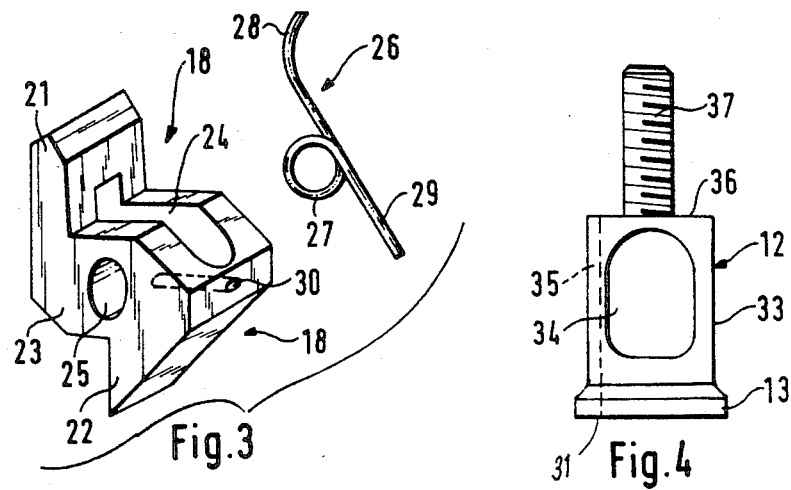
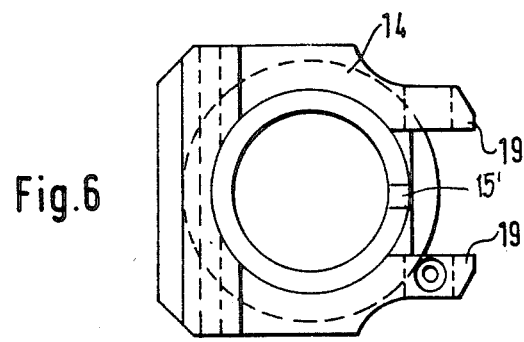
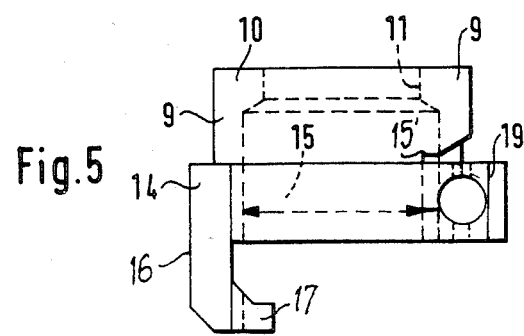

RETAINING DEVICE FOR A SURGICAL INSTRUMENT

CROSS-REFERENCE TO RELATED PATENTS

This application is related to U.S. Pat. No. 4,143,652, granted Mar. 13, 1979, entitled "Surgical Retaining Device", and U.S. Pat. No. 4,491,435, granted Jan. 1, 1985, and entitled "Jointed Stand".

BACKGROUND OF THE INVENTION

The present invention broadly relates to a retaining device or apparatus and, more specifically, pertains to a new and improved construction of a retaining device for holding a surgical instrument.

Generally speaking, the surgical retaining or holding device of the present invention comprises a holder block which is displaceably and selectively securable along and at a guide member, such as a guide rail. The holder block is provided with clamping elements for engagement with the guide rail. Furthermore, the retaining device is provided with a support rod for holding the surgical instrument or the like. This support rod is displaceable and positionally securable with respect to the holder block.

Wound hooks are a particular example of surgical instruments which, by means of the retaining device which expediently incorporates a number of articulatedly or hingedly coupled link members, are fixed or secured to a guide rail positioned along an operating table. It should be understood that instead of using wound hooks with such retaining devices other surgical instruments, such as speculars, wound spreaders, magnifying lenses, spatulas, holders for X-ray plates or X-ray cassettes and similar instruments that the surgeon deems necessary to perform the operation or his or her work may be mounted at the retaining device.

In the aforementioned U.S. Pat. No. 4,143,652, granted Mar. 13, 1979, there have been disclosed to the art such type of surgical retaining or holding devices for which there exists an increasing demand. They have been improved to such an extent that they are capable of arresting or positionally fixing larger wound hooks with adequate retention or holding force as, for instance, is necessary when performing more complicated surgical operations such as at the thorax and during abdominal surgery in order to positionally retain the edges of the surgical wound or incision with the requisite reliability.

In the course of development work these retaining or holding devices could be further improved such that the end of the articulated or link arm which carries the surgical instrument can now be positively or immovably held in position and is incapable of positionally shifting during the surgical operation.

A serious disadvantage or shortcoming of all of the heretofore known retaining or holding devices resides in the fact that these retaining devices comprise several mutually independent and different facilities or means, each serving for performing a specific function. One such facility or means may serve to displace and arrest the retaining device along the guide rail, whereas another may serve to adjust the elevational position of the surgical instrument by allowing for appropriate sliding of the support rod in the holder block and its retention thereat. Thus, the known retaining devices have a separate arrangement in order to clamp the holder block at the guide rail and which is accomplished with the aid of a tensioning or tightening lever, whereas a second clamping arrangement serves to fixedly clamp the support rod which is provided with the surgical instrument. A hand wheel serves to actuate the second clamping arrangement. This disadvantage is a considerable one, since during an operation it is usually required to move or displace the holder block along the guide rail as well as to re-position the elevational level or location of the wound hook. Additionally, the support rod of the known retaining devices can only be turned or rotated about its own lengthwise axis and can not be rotated and fixed with respect to an axis transverse thereto. Thus, the clamped portion of the support rod of the known retaining devices always extends perpendicular with respect to the guide rail located at the operating table.

SUMMARY OF THE INVENTION

Therefore with the foregoing in mind it is a primary object of the present invention to provide a new and improved construction of a retaining or holding device, especially a surgical retaining or holding device, which does not exhibit the aforementioned drawbacks and shortcomings of the prior art constructions.

Another and more specific object of the present invention aims at providing a new and improved construction of a retaining device or the like for surgical instruments in which the displaceable securing or clamping action of the retaining device along the stationary guide rail as well as the angular and translatory positioning and securing of the support rod is substantially simplified.

Still another important object of the present invention aims at the provision of a new and improved construction of a retaining device for surgical instruments which allows for a simplified yet highly reliable selective spatial positioning of the surgical instrument in a desired site for accomplishing a surgical operation and secure retention of the thus spatially positioned surgical instrument with a minimum of effort.

Yet a still further noteworthy object of the present invention aims at the provision of a new and improved construction of a retaining device for surgical instruments which contains relatively few structural parts for accomplishing a reliable and positive spatial positioning of the surgical instrument in a desired locality for the operating surgeon and by virtue of the simplified construction of the retaining device requires fewer parts to undergo a sterilization operation so that such sterilization operation is effectively simplified.

Yet a further significant object of the present invention aims at providing a new and improved construction of a retaining or holding device for surgical instructions and which is relatively simple in construction and design, extremely economical to manufacture, highly reliable in operation, not readily subject to breakdown and malfunction and requires a minimum of maintenance and servicing.

Now in order to implement these and still further objects of the present invention which will become more readily apparent as the description proceeds the surgical retaining device of the present invention is manifested by the features that clamping or gripping means are provided for displaceably securing the support rod. These clamping or gripping means, defining a clamping mechanism, are rotatable and arrestable in position with respect to the clamping elements of the holder block. The clamping or gripping means simultaneously actuate the clamping elements of the holder block when positionally arresting the support rod.

In this manner a substantial simplification is attained, since only one single actuating or activating means is necessary for actuating the clamping or gripping means for the support rod as well as the clamping elements of the holder block. In addition, an angular displacement of the support rod is now possible in a vertical plane extending substantially perpendicular to the lengthwise axis of the holder block. A still further advantage may be seen in the small number of parts or components as compared to the prior art devices. This affords a simpler and more efficient sterilization of such parts or components without the need for dismantling the same.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally used the same reference characters to denote the same or analogous components and wherein:

FIG. 2 shows a perspective view of a portion of the holder block and the clamping mechanism of the retaining or holding device depicted in FIG. 1 and illustrating the same in a dismantled and exploded view;

FIG. 3 shows in a perspective and exploded view certain details of the arrangement depicted in FIG. 2;

FIG. 4 shows a front view of the thrust sleeve of the arrangement of FIG. 2.

FIG. 5 shows a side view of part of the holder block of the retaining device; and FIG. 6 shows a plan view of FIG. 5.

DETAILED DESCRIPTION OF THE PREFERRED EMBODIMENTS

Figure 1:
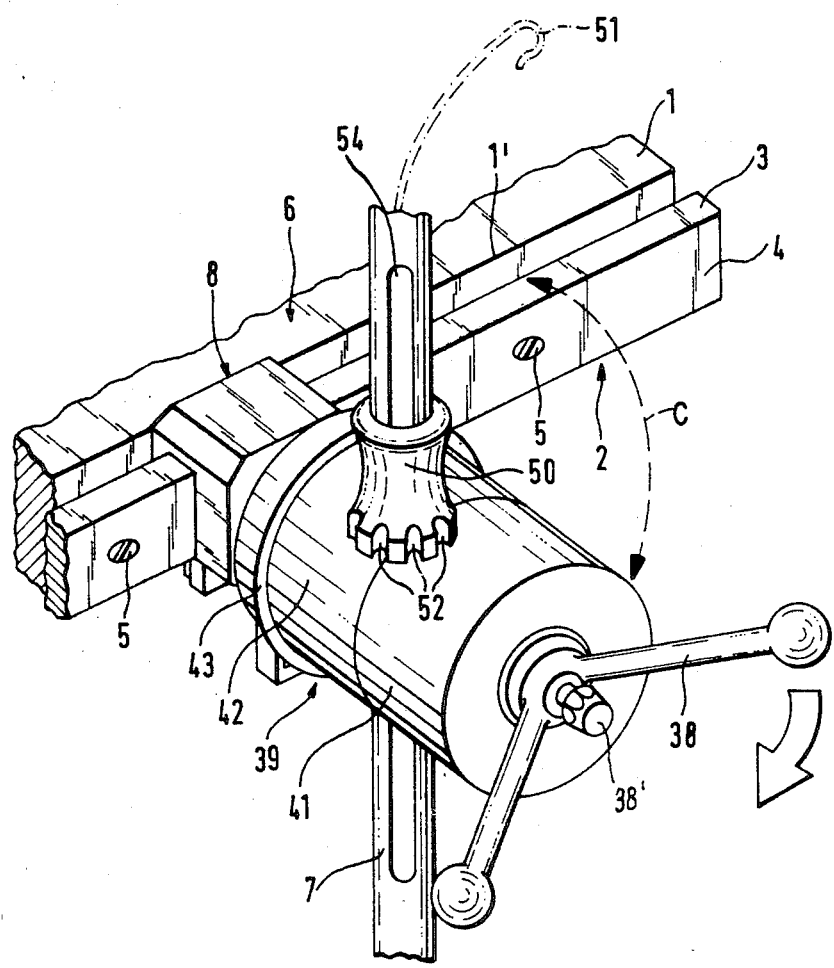
FIG. 1 shows a perspective view of a preferred embodiment of surgical instrument retaining or holding device constructed according to the present invention.
Figure 1A:
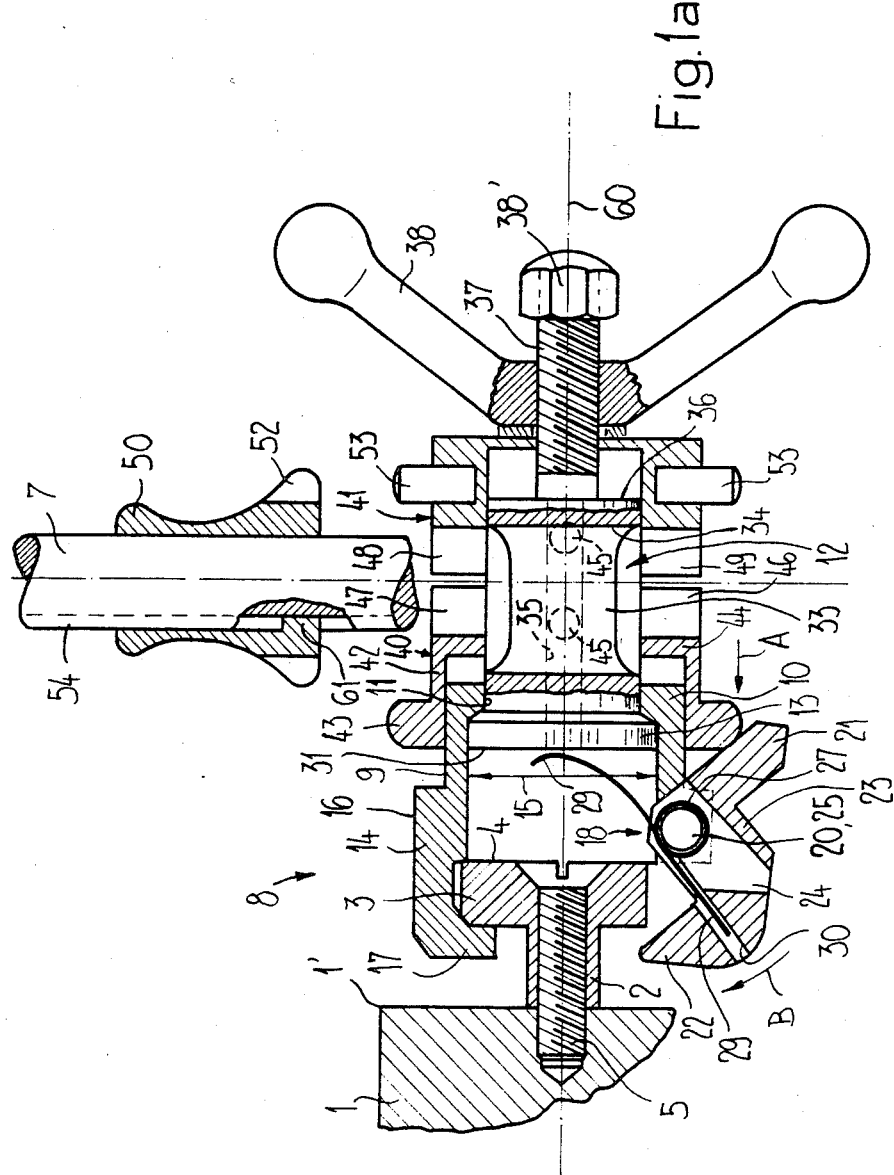
FIG. 1a illustrates on a somewhat enlarged scale and partially in cross-sectional view the retaining or holding device depicted in FIG. 1.

Describing now the drawings, it is to be understood that to simplify the showing thereof only enough of the structure of the surgical instrument retaining or holding device has been illustrated therein as is needed to enable one skilled in the art to readily understand the underlying principles and concepts of the present invention. Turning now specifically to FIGS. 1 and 1a of the drawings, the retaining or holding device 6 illustrated therein by way of example and not limitation will be seen to comprise a holder block 8 and a clamping or gripping mechanism 39. The holder block 8 is selectively displaceably fixed to an operating table 1 by means of a guide or clamp rail 2 which extends along a longitudinal edge or side 1' of the operating table 1. The guide rail 2 may, for example, possess a substantially T-shaped cross-section having a narrow horizontal face or surface 3 and a broader vertical face or surface 4. The guide rail 2 is fixedly connected or attached to the longitudinal edge or side 1' of the operating table 1 by means of, for example, screws 5 or equivalent fastening expedients appropriately spaced along the length of the guide rail 2.

The retaining or holding device 6 is, on the one hand, selectively displaceable along and fixable in desired position at the guide rail 2 and, on the other hand, serves to receive and positively hold an instrument support means here shown in the form of a support rod or supporting member 7. The support rod 7 can be positionally adjusted and positively locked in different elevational and angular positions in the retaining or holder device 6. The support rod 7 serves to hold an only schematically indicated surgical instrument 51 which may be constituted, for instance, by a wound hook. This support rod 7 is composed of individual mutually interlinked or articulated members of known construction.

The retaining or holder device 6 is attachable to and slidable along the guide rail 2 by means of the holder block 8 serving primarily as a guide element and position fixation element for the retaining device 6. The holder block 8 comprises as its guide element a substantially ring-shaped guide body 9 for the clamping or gripping mechanism 39 as will be discussed hereinafter. As will be recognized from FIG. 5, an inwardly projecting shoulder or collar 10 at one end of the guide body 9 forms an inner guiding bore or ring 11 in which there is guided a thrust sleeve or sleeve member 12 (FIG. 2) as will be further described hereinafter. FIG. 2 shows an end position of the thrust sleeve or sleeve member 12 in the guiding bore or ring 11. This end or terminal position of the thrust sleeve or sleeve member 12 depicted in FIG. 2 is that position where an outer shoulder 13 at one end of the thrust sleeve 12 abuts against the inwardly projecting shoulder or collar 10 of the guide body 9 during displacement of the thrust sleeve 12 in the guiding bore or ring 11. The shoulder or collar 13 thus serves to limit the stroke or displacement motion of the thrust sleeve 12.

The substantially ring-shaped or cylindrical guide body 9, at the side or end opposite the inwardly projecting shoulder 10, has merging therewith a substantially horseshoe-shaped or bifurcated body or part 14 which is advantageously integrally formed with the ring-shaped guide body 9. The horseshoe-shaped body or part 14 has an opening 15 possessing a substantially wedge-shaped projection 15' (see FIG. 5) and the ring-shaped or cylindrical guide body 9 is open-ended so that the thrust sleeve 12 can be appropriately inserted into the ring-shaped or cylindrical guide body 9. The horse-shoe shaped or bifurcated body or part 14 has an angular or cornered outer contour or configuration and is provided at a side surface 16 thereof with an inwardly extending fixed clamping jaw or jaw member 17 which, in conjunction with a pivotable clamping jaw or jaw member 18, constitute the clamping elements or means for clamping the retaining or holding device 6 to the guide rail 2. The pivotable clamping jaw 18 is pivotably journalled about a pivot pin 20 whose oppositely situated ends are mounted in two horn-like parts or protrusions 19 of the horseshoe-shaped or bifurcated body or part 14.

As shown in FIG. 3 the pivotable clamping jaw 18 comprises two mutually offset substantially parallel extensions or arms or arm members 21 and 22 which are interconnected to one another by a connection piece or body portion 23 which extends approximately perpendicular to both of these arms 21 and 22. The entire pivotable clamping jaw 18 is constructed as a massive single integral unit and is provided in the longitudinal central plane or middle thereof with a recess 24. A bore 25 extends transversely through the connecting piece or body portion 23. Furthermore, there is provided a spring or hairpin spring 26 having a spiraled body or coiled portion 27 and tensioning or biasing arms 28 and 29. The pivot pin 20 is inserted into the bore 25 and the spring 26 is located in the recess 24 such that the pivot pin 20 extends through the spiraled body or coiled portion 27 of the spring 26. Furthermore, there is provided another bore 30, terminating in the bottom portion or base of the recess 24, which serves to receive the tensioning or biasing arm 29 of the spring 26 (see FIG. 1a). The other, bent or angled biasing or tensioning arm 28 of the spring 26 contacts a bottom surface 31 of the thrust sleeve or sleeve member 12, thereby bounding or delimiting the one terminal or end position of the thrust sleeve or sleeve member 12. A clamping or set screw 32 secures the pivot pin 20 from dropping out of the bore 25. The set screw 32 is screwed into a corresponding threaded bore of one of the horn-like parts or protrusions 19 and projects into a corresponding transverse bore or borehole provided in the pivot pin 20.

By virtue of the construction as described hereinbefore there is obtained the result that the pivotable clamping jaw 18 can only be swiveled or pivoted in a clockwise direction as indicated by the arrow B in FIG. 1a against the force of the spring 26. This pivotable or swivelable motion is caused by an axial force A acting upon the extension or arm 21 of the pivotable clamping jaw 18 as will still be described more fully hereinafter. This axial force A causes the pivotable clamping jaw 18 to swivel in the clockwise direction B thereby clamping, in conjunction with the fixed clamping jaw 17, the holder block 8 of the retaining device 6 at the guide rail 2 located between these clamping jaws 17 and 18.

This cooperation or coaction of the fixed clamping jaw 17 with the pivotable clamping jaw 18 may be compared to a human hand, and the action of the pivotable clamping jaw 18 can be considered as resembling that of the thumb. Because of the inclined faces at the inside of both clamping jaws 17 and 18 the holder block 8 is pressed against the outer vertical face or surface 4 of the guide rail 2 during tensioning or tightening of the retaining device 6. Additionally, the special shape or configuration of the inner surfaces of the clamping jaws 17 and 18 enables the usage of an identical holder block 8 for all kinds of operating table guide rails 2. Such guide rails 2 may be standardized differently in different countries. It bears mentioning that the fixed clamping jaw 17 is substantially hook-shaped, enabling it to hook over or engage behind the horizontal face or surface 3 of the guide rail 2. Consequently, the retaining device 6 as a whole remains hangingly suspended on the guide rail 2 even when the pivotable clamping jaw 18 is not clampingly engaging the guide rail 2, thus avoiding an unintentional dropping of the retaining device onto the floor.

As best recognized by referring to FIGS. 1a, 2 and 4, the thrust sleeve or sleeve member 12 has a substantially cylindrical portion 33 provided with an elongated hole or opening 34. The cylindrical portion 33 further possesses a longitudinal groove 35. On a top surface 36 of the thrust sleeve or sleeve member 12 located opposite the bottom surface 31 thereof, a threaded bolt or threaded spindle 37 is axially attached to the thrust sleeve or sleeve member 12. Screwed onto the bolt 37 is a tightening nut or butterfly or wing nut 38 which serves as the actuating or activating means of the retaining device 6. A cap screw 38' or the like engaging with the threaded bolt 37 prevents a disengagement of the tightening nut 38 from the threaded bolt 37.

The thrust sleeve or sleeve member 12 coacts with a clamping or gripping mechanism 39. This clamping or gripping mechanism 39 comprises an inner or lower clamping or gripping part or head 40 and an outer or cover-like clamping or gripping head or part 41. The inner sleeve-shaped clamping or gripping head or part 40 has a cylindrical or ring-shaped portion 42 terminating in an outwardly projecting flange portion or rim 43 at one end thereof, whereas the other end is provided with an inwardly projecting flange portion or inner flange 44, the inside diameter of which corresponds to the outside diameter of the cylindrical portion 33 of the thrust sleeve or sleeve member 12. The inwardly projecting flange portion 44 is further provided with a guide pin or projection 45 which radially extends inwardly, projecting into the longitudinal groove 35 of the thrust sleeve or sleeve member 12. The inner or inside diameter of the cylindrical portion 42 corresponds to the outside diameter of the cylindrical guide body 9. With reference to FIG. 1a the inwardly projecting flange portion 44 has on its outer or right-hand side thereof two diametrically opposed and coaxially arranged recesses 46 and 47, each having a substantially semi-cylindrical or semi-circular cross-section. Together with correspondingly shaped semi-cylindrical or semi-circular recesses 48 and 49 provided in the outer or right-hand located cover-like clamping or gripping head 41 they constitute a passageway for the support rod 7. The recesses 46, 47, 48 and 49 serve as contact surfaces for gripping the support rod 7. The aforementioned passageway extends perpendicular to and intersects the lengthwise axis 60 of the holder block 8. The support rod 7, also extending through the elongated hole or opening 34 of the thrust sleeve or sleeve member 12, possesses a longitudinal groove 54 into which projects a key or pin 61 or the like which is provided at an externally toothed arresting sleeve 50 so that the latter may be displaceably but non-rotatably guided upon the support rod 7. The tooth gaps or spaces between the teeth 52 of the externally toothed arresting sleeve 50 cooperate with a pin 53 provided in the outer or cover-like clamping or gripping head or part 41 for adjustingly fixing the rotational position of the support rod 7.

In operation, as shown in FIG. 1, the holder block 8 is positioned onto the guide rail 2 such that this guide rail 2 is located between the fixed clamping jaw or jaw member 17 and the pivotable clamping jaw or jaw member 18. The support rod 7, directly or indirectly supporting the surgical instrument 51, extends through the passageway formed by the semi-circular or semi-cylindrical recesses 46, 47, 48 and 49 of the clamping or gripping mechanism 39 and through the elongated hole or opening 34 of the thrust sleeve or sleeve member 12. This thrust sleeve or sleeve member 12 is subjected to the action or force of the bent tensioning arm 28 of the spring or spring member 26. The outwardly projecting flange portion or rim 43 of the inner gripping head 40 is in abutting relationship with the extension or arm 21 of the pivotable clamping jaw 18. This is the open or unclamped position of the retaining device 6, i.e. of the holder block 8 as well as of the clamping or gripping mechanism 39, enabling the holder block 8 to slide or move along the guide rail 2 while the support rod 7 can elevationally slide in the clamping or gripping mechanism 39, and specifically within the inner or lower clamping part or head 40 and the outer cover-like clamping part or head 41. Both clamping or gripping heads or parts 40 and 41 bear against the inclined protruding arm 21 of the pivotable clamping jaw 18. This pivotable clamping jaw 18 is retained in its open position under the action of the spring 26. The clamping or gripping mechanism 39 together with the support rod 7 can be rotated or angularly displaced around or with respect to the ring-shaped guide body 9 such that the support rod 7 can be selectively angularly displaced in the direction of the double-headed arrow C in FIG. 1 within a vertical plane parallel to the guide rail 2 and substantially perpendicular to the threaded bolt or screw 37.

When the butterfly or wing nut 38 is now tightened, the inner or left-hand clamping part or gripping head 40 and the outer or right-hand clamping part or gripping head 41 shown in FIG. 1a, which are guided to be non-rotatable, are pressed against one another thus fixedly gripping and retaining the support rod 7 by means of their semi-circular recesses or bores 46, 47, 48 and 49. Simultaneously, both clamping parts or gripping heads 40 and 41 are conjointly slidingly moved along the thrust sleeve or sleeve member 12. The movement of the clamping parts or gripping heads 40 and 41 is rendered possible by virtue of the provision of the elongate hole or opening 34. This movement causes the flange portion or rim 43 of the inner clamping part or gripping head 40 to move in the direction of the arrow A (FIG. 1a), thereby exerting a force upon the extension or arm 21 which results in a rotational clockwise movement in the direction of the arrow B against the action of the spring 26. The pivoting motion of this pivotable clamping jaw 18 in relation to the fixed clamping jaw 17 causes the retaining or holder device 6 to be firmly clamped onto the guide rail 2. In this manner the entire retaining device 6 is fixed in a position determined by the user. Only the butterfly or wing nut 38 needs to be tighted in order to simultaneously grip and fix the support rod 7 in its desired position and to clamp the holder block 8 onto the guide rail 2. Loosening the wing nut 38 would result in simultaneously loosening or releasing these parts.

Loosening or release of the retaining device 6 is accomplished by turning the wing nut 38 in the opposite direction causing the pivotable clamping jaw 18 to swivel or pivot in the counterclockwise direction under the action of the spring 26. Conjointly therewith the counterclockwise pivotal or swivel movement of the arm 21 of the pivotable clamping jaw 18 causes the clamping parts or gripping heads 40 and 41 to be pushed outwardly or to the right in FIG. 1a along the cylindrical portion 33 of the thrust sleeve or sleeve member 12. In order to facilitate this outward movement the flange portion or rim 43 may be rounded. In continuing the loosening or release of the wing nut 38 the clamping parts or gripping heads 40 and 41 mutually separate, i.e. they are no longer tightly pressed together so that the support rod 7 is released and free to move in relation to the holder block 8.

Finally, it is deemed worthwhile mentioning that without in any way impeding the manipulation of the retaining device 6 a sterilized hood or the like may be clamped by the pivotable clamping jaw 18. By simply turning the wing nut 38 the surgical instrument can be selectively positioned in any desired position.

The entire retaining device can be sterilized without the need to disassemble the same in a simple manner in an autoclave or other appropriate sterilizing facility or piece of equipment, particularly since all parts or components are advantageously formed of stainless steel.

While there are shown and described present preferred embodiments of the invention, it is to be distinctly understood that the invention is not limited thereto, but may be otherwise variously embodied and practiced within the scope of the following claims.

What we claimed is:

1. A retaining device, especially for holding a surgical instrument, comprising:
    a holder block adapted to be displaceably securable along a guide rail;
    said holder block being provided with clamping elements for fixedly engaging said holder clock with said guide rail;
    support means for holding the surgical instrument and displaceably supported by said holder block;
    clamping means provided for said holder block and serving for allowing displacement of said support means and for arresting said support means in a desired position;
    said clamping means being rotatable with respect to said clamping elements;
    actuating means for simultaneously actuating said clamping means and said clamping elements during arresting of said support means in a desired position;
    said clamping means comprising a fixed clamping jaw and a movable clamping jaw;
    said holder block comprising a guide body for supporting said clamping means;
    said clamping means being displaceably and rotatably mounted at said guide body;
    said actuating means comprising tightening means cooperating with said clamping means and serving for simultaneously tightening said clamping means and clamping said clamping elements at the guide rail;
    said holder block comprising a substantially horseshoe-shaped body member;
    said fixed clamping jaw being arranged at said substantially horseshoe-shaped body member;
    said substantially horseshoe-shaped body member of said holder block further comprises two arm members;
    a pivot pin arranged between said two arm members;
    spring means disposed about said pivot pin;
    said movable clamping jaw being mounted upon said pivot pin for pivotable movement between an open position and a closed position;
    said movable clamping jaw being biased into said open position by said spring means;
    said guide body being provided at said substantially horseshoe-shaped body member and serving to displaceably and rotatably mount said clamping means;
    said clamping means comprising a bipartite clamping mechanism composed of two clamping parts; and
    each of said two clamping parts having a pair of coaxially arranged recesses extending transverse to said guide body.

2. The retaining device as defined in claim 1, wherein:
    said clamping means further comprises a thrust sleeve member projecting from said guide body for supporting said clamping means;
    said thrust sleeve member having an elongated hole for accommodating said support means;

said thrust sleeve member being provided with a threaded spindle extending through said clamping means; and said tightening means including a tightening member cooperating with said threaded spindle for tightening said clamping means.

3. The retaining device as defined in claim 1, wherein:

said movable clamping jaw has a recess extending around said pivot pin and serving to accommodate said spring means.

4. The retaining device as defined in claim 1, further including:

means for pivotably mounting said movable clamping jaw at said holder block;

said pivotably mounted clamping jaw contains a recess located in a longitudinal central plane of said pivotably mounted clamping jaw; and said recess serving to receive said spring means.

5. A retaining device, especially for holding a surgical instrument, comprising:

a holder block adapted to be displaceably securable along a guide rail;

said holder block being provided with clamping elements for fixedly engaging said holder block with said guide rail;

support means for holding the surgical instrument and displaceably supported by said holder block;

clamping means provided for said holder block and serving for allowing displacement of said support means and for arresting said support means in a desired position;

said clamping means being rotatable with respect to said clamping elements;

actuating means for simultaneously actuating said clamping means and said clamping elements during arresting of said support means in a desired position;

said holder block having a lengthwise axis;

said clamping means comprising two clamping heads;

each of said two clamping heads having means defining contacting surfaces for engaging said support means therebetween;

said contacting surfaces of said two clamping heads defining a passageway for guiding said support means; and said passageway extending substantially transversely with respect to said lengthwise axis of said holder block.

6. A retaining device, especially for holding a surgical instrument, comprising:

a holder block adapted to be displaceably securable along a guide rail;

said holder block being provided with clamping elements for fixedly engaging said holder block with said guide rail;

support means for holding the surgical instrument and displaceably supported by said holder block;

clamping means provided for said holder block and serving for allowing displacement of said support means and for arresting said support means in a desired position;

said clamping means being rotatable with respect to said clamping elements;

actuating means for simultaneously actuating said clamping means and said clamping elements during arresting of said support means in a desired position;

said clamping means comprising a fixed clamping jaw and a movable clamping jaw;

said holder block comprising a guide body for supporting said clamping means;

said clamping means being displaceably and rotatably mounted at said guide body;

said actuating means comprising tightening means cooperating with said clamping means and serving for simultaneously tightening said clamping means and clamping said clamping elements at the guide rail;

said movable clamping jaw having an arm extending in the direction of the guide body;

means for pivotably mounting said movable clamping jaw at said holder block;

said clamping means comprising a clamping part provided with a rim; and said rim bearing against said pivotably mounted clamping jaw upon tightening of said clamping means so as to pivot said pivotably mounted clamping jaw in a predeterminate closing direction for engagement with said guide rail.

7. A retaining device, especially for holding a surgical instrument, comprising:

a holder block adapted to be displaceably securable along a guide rail;

said holder block being provided with clamping elements for fixedly engaging said holder block with said guide rail;

support means for holding the surgical instrument and displaceably supported by said holder block;

clamping means provided for said holder block and serving for allowing displacement of said support means and for arresting said support means in a desired position;

said clamping means being rotatable with respect to said clamping elements;

actuating means for simultaneously actuating said clamping means and said clamping elements during arresting of said support means in a desired position;

said clamping means comprising a substantially sleeve-shaped part and a cover-shaped part;

said sleeve-shaped part having an outer rim;

said sleeve-shaped part comprising a substantially cylindrical body portion bounded by said outer rim;

said sleeve-shaped part having an end situated remote from said outer rim and confronting said cover-shaped part;

said end of said sleeve-shaped part which confronts said cover-shaped part possesses an inner flange containing diametrically oppositely situated coaxial substantially semi-circular recesses and a guide pin;

said clamping means further comprising a thrust sleeve member having a longitudinal groove; and said guide pin engaging with said longitudinal groove in order to fix said sleeve-shaped part and said cover-shaped part in a desired rotational position with respect to said thrust sleeve member.

* * * * *